United States Patent [19]

Di Schiena

[11] Patent Number: 4,565,811

[45] Date of Patent: Jan. 21, 1986

[54] SODIUM SALT OF URSODEOXYCHOLIC SULPHATE

[75] Inventor: Michele G. Di Schiena, Milan, Italy

[73] Assignee: Istituto Biologico Chemioterapico "ABC" S.p.A., Turin, Italy

[21] Appl. No.: 582,522

[22] Filed: Feb. 22, 1984

[30] Foreign Application Priority Data

Feb. 24, 1983 [IT] Italy ................................ 19737 A/83

[51] Int. Cl.$^4$ ........................... A61K 31/56; C07J 7/00
[52] U.S. Cl. .................................... 514/182; 260/397.1
[58] Field of Search ...................... 260/397.1; 424/238; 514/182

[56] References Cited

U.S. PATENT DOCUMENTS

| 4,406,688 | 4/1984 | Scolastico | 260/397.1 |
| 4,425,274 | 1/1984 | Guillemette | 260/397.1 |
| 4,439,366 | 3/1984 | Scolastico et al. | 260/397.1 |
| 4,486,352 | 12/1984 | Giordano et al. | 260/397.1 |

OTHER PUBLICATIONS

Chemical Abstracts, vol. 97, (No. 5), Par. 39, 222(b).

*Primary Examiner*—Elbert L. Roberts
*Attorney, Agent, or Firm*—Oblon, Fisher, Spivak, McClelland & Maier

[57] ABSTRACT

A new compound of the general formula I:

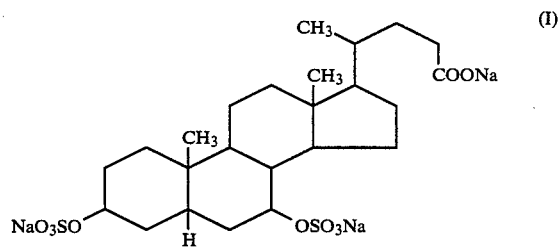

obtained from the ursodeoxycholic acid, soluble in water and its pharmaceutical compositions.

3 Claims, No Drawings

SODIUM SALT OF URSODEOXYCHOLIC SULPHATE

The present invention relates to the new sodium salt of ursodeoxycholic O-sulphate, hereinbelow called sodium ursosulphate.

The new compound of the invention has the following general formula I:

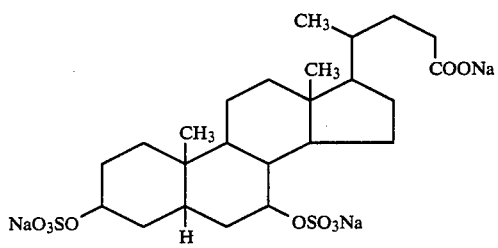

Ursodeoxycholic acid and its use in therapy is already known in the literature (J. Biochem. Japan 7,505, (1927); Merck Index 9th Ed.). This compound is, in fact, a pharmaceutical agent effective in the qualitative and quantitative alterations of the biligenetic function, also including those having the bile saturated with cholesterol: in these cases ursodeoxycholic acid prevents the formation of cholesterol stones and it is also able to dissolve under suitable conditions the radiotransparent stones, if present.

Ursodeoxycholic acid is also used in the dispeptic painful symptomatology from cholecistopatia with or without calcolosis, in the biliary discinesies and connected syndromes, in the lipemic alterations due to the increase of cholesterol and/or triglycerides.

The daily dosage is 150–750 mg by oral route. Both ursodeoxycholic acid and its sodium salt are pratically insoluble in water. This characteristic limits their therapeutic use to the solid formulations only, such as capsules and tablets.

As it is well known, these formulations are not always accepted by certain patients either for their difficulty to be swallowed or for their gastric intollerance.

Moreover capsules and tablets are not very suitable to a flexible posology.

The new compound of the invention, sodium ursosulphate, is characterized by the property of being very soluble in water.

Also the free acid, ursodeoxycholic O-sulphate, is very soluble in water: however, owing to its very high acidity, it is preferably used in the form of a salt, such as the new compound of the present invention.

Since the toxicity of sodium ursosulphate does not show any significative differences and maintains the values already known for ursodeoxycholic acid, this new compound is successfully employed in the therapy of the clinic symptomatology wherein ursodeoxycholic acid is already used.

The more useful and advantageous pharmaceutical preparations for the administration of the new compound of the invention are all the liquid formulations, such as syrups (including extemporary forms), drops, monodose ampouls. These liquid formulations allow to modify the posology of the new compound in accordance with the therapeutic case, the age of patients, the necessity to use an attack or maintenance therapy: it is possible, therefore, to perform the flexibility of the therapeutic dosage.

The new compound can be advantageously used also for preparing other oral pharmaceutical formulations, such as gelatine capsules, tablets (including gastro-resistant), emulsions, suspensions and granulates.

In addition to the high advantage of that solubility of the product of the invention, it has been surprisingly found that sodium ursosulphate (US) displays an activity in some cases higher than that of ursodeoxycholic acid (UA).

Pharmaco-toxicological trials, carried out on the product of the invention in comparison with UA, are following reported.

Action on the hyperdislipidemia caused by Triton WR-1339 in the rat

Albinus rats (Witar) of 300–320 g each, having been fed only with water "ad libitum" for 12 hours, were treated with US and UA, by oral route, 4 hours before and 15 hours after the administration intraperitenously of Triton WR-1339 at the dosage of 300 mg/kg in 10 ml/kg of physiologic solution at 0.9%.

US and UA dosages were 25, 50 and 100 mg/kg respectively and the rats were divided in the following groups of 10 animals each.

Group 1: Controls treated with 10 ml/kg of physiological solution at 0.9% orally.

Group 2: Controls treated with 300 mg/kg of Triton WR-1339 i.p. and 10 ml/kg of carboxy methyl cellulose (CMC) at 0.5%.

Group 3, 4 and 5: UA at 25, 50 and 100 mg/kg respectively suspended in 10 ml/kg of CMC at 0.5%.

Groups 6, 7 and 8: US at 25, 50 and 100 mg/kg respectively dissolved in 10 ml/kg of physiologic solution.

The following Tables 1 and 2 list the results of blood-tests from addominal aorta of rats sacrificed 5 hours after the last treatment:

TABLE 1

US and UA action inhibiting the hyperdislipidemia from Triton WR-1339 in the rat.

| Groups | Dose | Total cholesterol Average ± SD mg/100 ml serum | Inhibition in comparison with Group 2 in % | Triglycerids Average ± SD mg/100 ml serum | Inhibition in comparison with Group 2 in % | Total lipids Average ± SD mg/100 ml serum | Inhibition in comparison with Group 2 in % |
|---|---|---|---|---|---|---|---|
| 1 | — | 66,4 ± 8,81 | — | 88,28 ± 17,06 | — | 442,28 ± 49,68 | — |
| 2 | 300 mg/kg i.p. | 296,0 ± 32,24 | — | 1312,28 ± 95,15 | — | 3818,4 ± 391,09 | — |
| 3 | 25 mg/kg os | 244,8 ± 34,5* | −15,9% | 1167,14 ± 180,5* | −11,0% | 3011,4 ± 513,6** | −21,1% |
| 4 | 50 mg/kg os | 175,47 ± 54,26** | −40,7% | 893,6 ± 298,1** | −31,9% | 2517,3 ± 557,6** | −34,1% |
| 5 | 100 mg/kg os | 155,2 ± 50,3** | −47,6% | 628,8 ± 223,0** | −52,1% | 2241,14 ± 517,4** | −41,3% |
| 6 | 25 mg/kg os | 220,8 ± 36,4** | −25,4% | 1040,6 ± 91,08** | −20,7% | 2697,1 ± 706,8** | −29,4% |
| 7 | 50 mg/kg os | 163,2 ± 25,7** | −44,3% | 654,3 ± 206,5** | −50,1% | 1972,6 ± 550,0** | −48,4% |

TABLE 1-continued

US and UA action inhibiting the hyperdislipidemia from Triton WR-1339 in the rat.

| Groups | Dose | Total cholesterol Average ± SD mg/100 ml serum | Inhibition in comparison with Group 2 in % | Triglycerids Average ± SD mg/100 ml serum | Inhibition in comparison with Group 2 in % | Total lipids Average ± SD mg/100 ml serum | Inhibition in comparison with Group 2 in % |
|---|---|---|---|---|---|---|---|
| 8 | 100 mg/kg os | 147,2 ± 31,3** | −50,3% | 583,4 ± 121,1** | −55,5% | 1949,7 ± 273,9** | −48,9% |

*P < 0,05
**P < 0,001

TABLE 2

US and UA action inhibiting the hyperdislipidemia from Triton WR-1339 in the rat.

| Groups | Dose | Alfa-Lipoproteins Average ± SD mg/100 ml serum | Increase towards Group 2 | Beta-Lipoproteins Average ± SD mg/100 ml serum | Inhibition towards Group 2 | Beta/alfa ratio Average ± SD mg/100 ml serum | Inhibition towards Group 2 |
|---|---|---|---|---|---|---|---|
| 1 | — | 33,14 ± 4,12 | — | 33,25 ± 8,42 | — | 1,06 ± 0,38 | — |
| 2 | 300 mg/kg i.p. | 22,4 ± 3,3 | — | 273,6 ± 32,5 | — | 12,47 ± 2,64 | — |
| 3 | 25 mg/kg os | 27,6 ± 9,8* | +23,2% | 221,17 ± 38,4* | −19,1% | 8,95 ± 3,5* | −28,2% |
| 4 | 50 mg/kg os | 41,7 ± 11,3** | +86,1% | 133,7 ± 60,4** | −51,2% | 3,88 ± 1,73** | −68,8% |
| 5 | 100 mg/kg os | 39,64 ± 11,4** | +76,8% | 115,5 ± 58,7** | −57,7% | 3,41 ± 2,29** | −72,6% |
| 6 | 25 mg/kg os | 29,2 ± 6,7* | +30,4% | 191,5 ± 42,1** | −29,9% | 7,23 ± 3,6** | −42,0% |
| 7 | 50 mg/kg os | 39,32 ± 5,5** | +75,4% | 123,8 ± 27,7** | −54,7% | 3,15 ± 1,1** | −74,7% |
| 8 | 100 mg/kg os | 44,8 ± 8,5** | +100% | 102,3 ± 36,9** | −72,6% | 2,46 ± 1,2** | −80,3% |

*P < 0,05
**P < 0,001

From the above results it appears that the activity inhybiting the hyperdislipidemia caused by Triton WR-1339 depends on the dosage both in US and in UA. Moreover, it surprisingly appears that US is more active than UA in all the considered tests owing to its complete solubility which increases the adsorption and the bioavailability of product.

Acute toxicity of sodium ursosulphate was tested in rats by administering the different doses of the compound directly in a physiologic solution at 0.9% in a volume either of 10 ml/kg by oral route through a probe directly to the stomach or of 5 ml/kg intraperitoneally or intravenously.

The dosages administered to groups of 10 animals each are reported in the following Tables 3 to 5 together with the symptomatology observed for a period of 8 days. In all the tests, the $LD_{50}$ was not reached up to the administered doses.

TABLE 3

Acute toxicity of US in the rat by oral administration

| Dose mg/kg | Died animals | Mortality % | Symptomatology |
|---|---|---|---|
| 1000 | 0 | 0 | N |
| 2000 | 0 | 0 | N |
| 3000 | 0 | 0 | D |
| 4000 | 0 | 0 | D |
| 5000 | 2 | 20 | D |
| 6000 | 4 | 40 | D |

N = none
D = depression

TABLE 4

Acute toxicity of US in the rat by intraperitoneal administration

| Dose mg/kg | Died animals | Mortality % | Symptomatology |
|---|---|---|---|
| 500 | 0 | 0 | N |
| 600 | 0 | 0 | N |
| 700 | 0 | 0 | D |
| 800 | 0 | 0 | D |
| 900 | 2 | 10 | D |

N = none
D = depression

TABLE 5

Acute toxicity of US in the rat by intravenous route

| Dose mg/kg | Died animals | Mortality % | Symptomatology |
|---|---|---|---|
| 400 | 0 | 0 | N |
| 500 | 0 | 0 | N |
| 600 | 0 | 0 | D |
| 650 | 1 | 10 | D + C |
| 700 | 1 | 10 | D + C |
| 750 | 2 | 20 | D + C |

N = none
D = depression
C = chronic convulsions

The preparation of the new compound of the invention is carried out according to the methods known in the art, such as by reacting ursodeoxycholic acid in anhydrous pyridine with gaseous sulphuric anhydride.

Object of the invention is, particularly, a vary effective and simple method consisting of using the solid complex pyridine-sulphuric anhydride.

According to this method ursodeoxycholic acid is dissolved in N,N-dimethylformamide and then reacted with the solid complex pyridine-sulphuric anhydride in the ratio of 1.95–2.1 Mol (preferably 2 Mol) of this complex to 1 Mol of ursodeoxycholic acid.

The reaction temperature is from 0° to 100° C., preferably 20°–30° C.

After elimination of the dimethylformamide, for instance by distillation in vacuo, the new compound thus obtained in the acid form is treated with an aqueous, alcoholic or aqueous-alcoholic solution of sodium hydroxide to obtain the corresponding sodium ursosulphate. Preferred alcohols are those wherein sodium hydroxide is soluble, such as methanol or ethanol. Other sodium compounds can be advantageously used, such as sodium bicarbonate, sodium carbonate or sodium-2-ethylhexanoate.

Sodium ursosulphate is then separated, in the solid form, by method commonly used, for instance crystallization, precipitation from solvents wherein the compound is insoluble, evaporation either in vacuo, or not, liophilization or spray-drying.

The following Examples illustrate but do not limit the invention.

EXAMPLE 1

3.92 g of ursodeoxycholic acid, dissolved in 50 ml of anhydrous dimethylformamide, were added with 3.20 g of the complex pyridine-sulphuric anhydride maintaining under stirring for 12 yours at 20° C.

N,N-dimethylformamide is evaporated off in vacuo and the oily residue, consisting of ursosulphate acid being very soluble in water with acid reaction, is reacted with 30 ml of 1N sodium hydroxide.

After stirring, the aqueous solution is concentrated in vacuo to small volume and treated with 100 ml of methanol.

The turbid solution is filtered and the limpid filtrate is evaporated in vacuo to a small volume and added with 200 ml of acetone. The product crystallized under stirring, it is separated by filtration and dried in the air. Yield 4.8 g. Sodium ursosulphate thus obtained is very soluble in water. The NMR analysis correspond to the chemical structure searched.

The conductimetric analysis (for the acid, sulphate and carboxylic groups) has the expected values.
H'-NMR analysis of the sample

| Sodium ursosulphate in D$_2$O | |
|---|---|
| 0.71 (S) p.p.m. (in respect with TSP) | methyl linked to 21 - position |
| 1.00 (S) p.p.m. (in respect with TSP) | two methyl group in 18 - and 19 - position |
| from 2.66 to 0.33 (S) (in respect with TSP) | Addition of not well-indentified multiplets |
| 3.57 (S) p.p.m. (in respect with TSP) | Hydrogen atoms linked to C in 3 - and 7 - position |

Conductimetric analysis $$\text{Sodium ursosulphate } R = \frac{SO_3^-}{COO^-} = 2.1$$

EXAMPLE 2

Preparation of monodose ampouls 0.150 g of sodium ursosulphate are dissolved in 10 g of 70% sorbitol and 0.5 mg of black-current flavour. The solution is used for preparing monodose ampouls.

EXAMPLE 3

Preparation of syrups 1 g of sodium ursosulphate is dissolved in 36 g of sugar, 10 g of sorbitol, 0.0005 g of peppermint, g 0.1 of methyl p-oxybenzoate, 5 g of ethyl alcohol, water q.s. to 100 g. One spoon of syrup=10 g=0.10 g of sodium ursosulphate.

EXAMPLE 4

Oral Drops 10 g of sodium ursosulphate are dissolved in 50 ml of 70% sorbitol, 0.180 g of methyl p-oxybenzoate and water q.s. to 100 g.

20 drops=1 g=0.10 g of sodium ursosulphate.

EXAMPLE 5

Preparation of syrup 2 g of sodium ursosulphate are dissolved in 36 g of sugar, 0.0005 g of peppermint, 0.1 g of methyl p-oxybenzoate, 5 g of ethyl alcohol and water q.s. to 100 g.

One spoon of syrup=10 g=0.20 g of sodium ursosulphate.

EXAMPLE 6

Oral Drops 40 g of sodium ursosulphate are dissolved in 50 ml of 70% sorbitol, 0.180 g of methyl p-oxybenzoate and water q.s. to 100 g.

20 drops=1 g=0.40 g of sodium ursosulphate.

I claim:

1. Trisodium salt of ursodeoxycholic O-sulphate having the following general formula I:

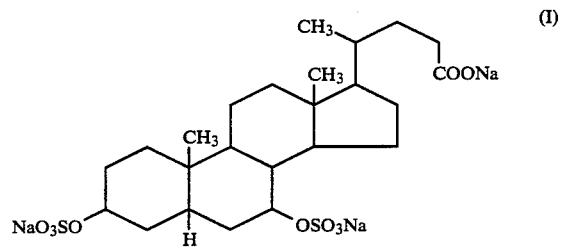

2. A process for preparing the compound of the above general formula (I), characterized in that ursodesoxycholic acid, dissolved in dimethylformamide is reacted at a temperature ranging from 0° to 100° C., preferably 20° C., with the solid complex pyridine-sulphuric anhydride in a molar ratio ranging from 1.95 to 2.1 Mol, preferably 2 Mol, the reaction mixture is allowed to stand for 12 hours, the solvent is evaporated off in vacuo, the resulting oily residue, consisting of ursodeoxycholic O-sulphate as free acid, is neutralized with a 1N aqueous, aqueous-alcoholic or alcoholic solution of sodium hydroxide, and acetone is added to the filtered solution to crystallize the compound of the above formula I which is separated by filtration and dried in the air.

3. A pharmaceutical composition comprising the compound of claim 1 and a pharmaceutically acceptable carrier.

* * * * *